United States Patent [19]

Haeckel et al.

[11] 4,202,938
[45] May 13, 1980

[54] PROCEDURE FOR THE QUANTITATIVE DETERMINATION OF HYDROGEN PEROXIDE CONCENTRATION IN AQUEOUS SOLUTIONS

[75] Inventors: Rainer Haeckel; Fritz Heinz, both of Hanover, Fed. Rep. of Germany

[73] Assignee: Human Gesellschaft mbH für Biotopanalytic und Biotopschutz, Fed. Rep. of Germany

[21] Appl. No.: 857,907

[22] Filed: Dec. 6, 1977

Related U.S. Application Data

[63] Continuation of Ser. No. 673,700, Apr. 5, 1976, abandoned.

[51] Int. Cl.$^2$ ............................................. G01N 31/14
[52] U.S. Cl. ....................................... 435/10; 435/11; 435/14; 435/19; 435/26; 435/27
[58] Field of Search ................ 195/103.5 R, 103.5 C, 195/103.5 U; 435/10, 11, 14, 19, 26, 27

[56] References Cited

U.S. PATENT DOCUMENTS 3,862,012  1/1975  Stork .............................. 195/103.5 U

OTHER PUBLICATIONS

Lundquist, "Determination with Aldehyde Dehydrogenase," *Methods of Enzymatic Analysis*, Bergmeyer, ed., Academic Press, Inc., (1974), pp. 1509–1513.
Kageyama, *Clin. Chem. Acta*, 31, (1971), pp. 421–426.

*Primary Examiner*—Esther M. Kepplinger
*Attorney, Agent, or Firm*—Miller & Prestia

[57] ABSTRACT

A novel procedure for the quantitative determination of hydrogen peroxide concentration in aqueous solutions is described. This is characterized by reacting hydrogen peroxide with an alcohol in the presence of the catalyst catalase and by reacting the resulting aldehyde in the presence of aldehyde dehydrogenase with NAD or NADP followed by determination of NADH or NADPH formed.

7 Claims, No Drawings

PROCEDURE FOR THE QUANTITATIVE DETERMINATION OF HYDROGEN PEROXIDE CONCENTRATION IN AQUEOUS SOLUTIONS

This is a continuation of application Ser. No. 673,700, filed Apr. 5, 1976 now abandoned.

In medical laboratories, particularly in clinical chemistry, the quantative determination of hydrogen peroxide plays an increasingly important role as an indicator reaction in different analytical methods. For instance, glucose in the form of blood sugar can be converted into gluconic acid and hydrogen peroxide with the aid of glucose oxidase, uric acid can be converted with the help of uricase into allantoin, carbon dioxide and hydrogen peroxide by reaction with 2 mol water and 1 mol oxygen, and cholesterol can be converted with the help of cholesterol oxidase into $\Delta^4$-cholestenone and hydrogen peroxide by reacting with 1 mol water and 1 mol oxygen. Thus by way of determining hydrogen peroxide the concentration of glucose, uric acid or cholesterol can be measured in aqueous solutions. For this purpose principally two indicator reactions have been employed up to now.

In the determination of glucose, the hydrogen peroxide formed was reacted with a reduced hydrogen donor, e.g. o-dianisidine, under the catalytic influence of peroxidase. The concentration of the resulting dye ordinarily was determined by the light absorption of the reaction mixture at a specific wave length. However, the extinction coefficient of the resulting dye being unknown, it was necessary in each test series to run a standard solution, thus making for a cumbersome and demanding procedure. Furthermore, the results of this method are subject to interference by specific substances such as ascorbic acid, so that it could not be used, for instance, for urine analysis.

For the determination of uric acid or cholesterol the conversion of the hydrogen peroxide formed by reacting the latter with methanol under the influence of catalase has been a familiar indicator reaction in which formaldehyde and water are formed. The formaldehyde was further reacted with $CH_3COCH_2COCH_3$ and ammonia, with formation of 3,5-diacetyl.1,4-dihydrolutidine. This dye in turn was measured photometrically, using light of the wave length 410 nm.

Here also the extinction coefficient of the dye is not known, so that it was again necessary to run a standard solution with test series. Furthermore, the reaction is very slow; in the case of serum analysis it requires about 60 minutes. Also interference effects were noted in the presence of high concentrations of ascorbic acid.

Thus the problem underlying our invention was to obtain a method for the quantitative determination of hydrogen peroxide in aqueous solutions involving the photometric measurement of a reaction product of known extinction coefficient so that simultaneous analysis of a standard solution becomes unnecessary. Another objective of the invention was to obtain a rapid course of the reaction in the determination, and still another was to obtain a method which is not subject to interference by other substances which occasionally or frequently occur in biological media, such as in urine and serum analyses.

In our invention the procedure for the quantitative determination of hydrogen peroxide concentration in aqueous solutions, particularly in biological media, is characterized by an initial step in which hydrogen peroxide in aqueous solution in the presence of the catalyst catalase is reacted with an alcohol with formation of an aldehyde, with subsequent reaction of the latter, under catalysis by aldehyde dehydrogenase, with the oxidized form of nicotinamide-adenine-dinucleotide (NAD) or nicotinamide-adenine-dinucleotide-phosphate (NADP) and final determination of the concentration of the reduced forms of these compounds (NADH or NADPH). It is convenient to use photometry for the determination of the NADH or NADPH concentrations in the final solution, best at a wave length of about 340 nm. Since the extinction coefficient of NADH or NADPH is known it is not necessary to run a companion analysis of a standard solution of the substance to be determined. Instead, the concentration C can be obtained directly from the equation $f = C/E$ in which f is a test-dependent constant and E the experimentally determined extinction. Since the companion analyses of standard solutions are superfluous this method is substantially more simple and rapid than the known methods.

Another advantage is that the course of reaction is rapid and that the reactions are not disturbed by interfering substances, particularly not by those which occur in ordinary biological media such as urine and serum specimens. For the first reaction step it is advisable to use an alcohol with 1 to 3 carbon atoms, preferentially ethanol since with this alcohol the reaction runs particularly fast and, specifically, more rapidly than with methanol or propanol. The two reactions used in the method of our invention may be described by the following reaction engines:

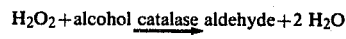

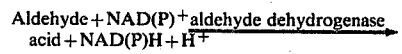

The following aldehyde dehydrogenases can be used:
Aldehyde: NAD oxidoreductase E.C. 1.2.1.3.
Aldehyde: NADP oxidoreductase E.C. 1.2.1.4.
Aldehyde: NAD(P) oxidoreductase E.C. 1.2.1.5.
Benzaldehyde: NADP oxidoreductase E.C. 1.2.1.7.
Betainaldehyde: NAD oxidoreductase E.C. 1.2.1.8.
Formaldehyde: NAD oxidoreductase E.C. 1.2.1.1.

Obviously the individual reaction steps can be carried out successively, for instance by adding NAD or NADP to the mixture after the first reaction has been completed. Still, it is advisable that both reactions run simultaneously in the same reaction medium, by adding to it from the very beginning all reaction ingredients and catalysts required for both reaction steps.

The proposed method is particularly suitable for the quantitative determination of uric acid, glucose (blood sugar), cholesterol and cholesterol esters. It is a very special advantage that with this method cholesterol and cholesterol esters can be analyzed separately.

In using the procedure of the invention for the quantitative determination of these compounds, namely uric acid, glucose, cholesterol or chloesterol esters, it is particularly advisable and simple to have the formation of hydrogen peroxide—by catalytic conversion of the substance to be determined—proceed in the same medium simultaneously with the above-named two catalytic reactions. For the determination of uric acid this is the above-mentioned conversion to allantoin and hydrogen peroxide by uricase. Thus it would be useful to add to the uric acid solution all reaction ingredients and catalysts required for the hydrogen peroxide determination, namely alcohol, NAD or NADP, catalase and aldehyde dehydrogenase, and then to get the following three-step reaction process started by the addition of uricase:

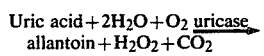
Uric acid + 2H$_2$O + O$_2$ $\xrightarrow{uricase}$ allantoin + H$_2$O$_2$ + CO$_2$

H$_2$O$_2$ + alcohol $\xrightarrow{catalase}$ aldehyde + 2H$_2$O

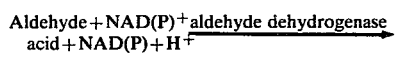
Aldehyde + NAD(P)$^+$ $\xrightarrow{aldehyde\ dehydrogenase}$ acid + NAD(P) + H$^+$ In the measurement of uric acid according to our invention with the aid of quantitative hydrogen peroxide determination, one obtains the surprising result that the uric acid which in blood is tied to protein is being determined 100%, while with the presently known analytic methods uric acid can be obtained maximally to the extent of only 95%, thus leading to inaccurate analytical results since one cannot say precisely to what percentage uric acid was determined.

The above considerations for the determination of uric acid also apply to the methods for the determination of glucose, cholesterol and cholesterol ester. In these cases also it is convenient to provide for the catalytic conversion of glucose, cholesterol or cholesterol ester in the same medium together with the reactions of hydrogen peroxide with alcohol and of the resulting aldehyde with NAD or NADP. In these determinations the following reactions take place in the medium:

Glucose + H$_2$O + O$_2$ $\xrightarrow{glucoseoxidase}$ gluconic acid + H$_2$O$_2$ H$_2$O$_2$ + alcohol $\xrightarrow{catalase}$ aldehyde + 2H$_2$O

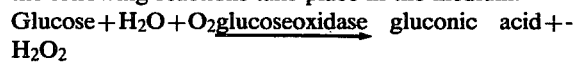
Aldehyde + NAD(P)$^+$ $\xrightarrow{aldehyde\ dehydrogenase}$ acid + NAD(P)H + H$^+$

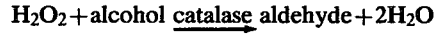
Cholesterol + H$_2$O$_2$ + O$_2$ $\xrightarrow{cholesteroloxidase}$ H$_2$O$_2$ + $\Delta^4$-cholestenone

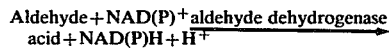
H$_2$O$_2$ + alcohol $\xrightarrow{catalase}$ aldehyde + 2H$_2$O

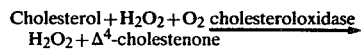
Aldehyde + NAD(P)$^+$ $\xrightarrow{aldehyde\ dehydrogenase}$ acid + NAD(P)H + H$^+$

Cholesterol ester + H$_2$O $\xrightarrow{cholesterolesterase}$ cholesterol + fatty acid

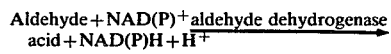
Cholesterol + H$_2$O + O$_2$ $\xrightarrow{cholesteroloxidase}$ H$_2$O$_2$ + $\Delta^4$-cholestenone

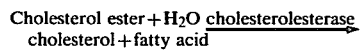
H$_2$O$_2$ + alcohol $\xrightarrow{catalase}$ aldehyde + 2H$_2$O

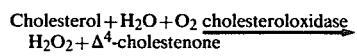
Aldehyde + NAD(P)$^+$ $\xrightarrow{aldehyde\ dehydrogenase}$ acid + NAD(P)H + H$^+$

EXAMPLE

This example is concerned with the determination of uric acid concentration. The following reagent solutions were used:
1. Pyrophosphate buffer: Tetra-sodium diphosphate-10-hydrate (E. Merck, Darmstadt, Order No. 6591) 0.1 mol/l, pH = 8.6
2. Catalase (Boehringer-Manrheim GmbH, Order No. 15674) 20 mg/ml
3. Uricase (Boehringer-Mannheim GmbH, Order No. 15074) 2 mg/ml. A dilution is made every day: 20 µl + 200 µl twice-distilled water.
4. NAD solution (Boehringer-Mannheim GmbH, Order No. 15300) 10 mg/ml
5. Ethanol (E. Merck AG, Darmstadt, Order No. 970)
6. Aldehyde dehydrogenase E.C. 1.3.1.2., isolated form liver according to Leicht (3), specific activity: 0.5 U/mg protein.

Before each series a reaction mixture was made up from the solutions 1,2,4,5 and 6 in the following proportions:
Pyrophosphate buffer: 500 parts
Catalase: 0.5 parts
NAD solution: 20 parts
Ethanol: 40 parts
Aldehyde dehydrogenase: about 25 U/ml From this reaction mixture one pipettes 500 µl into a semimicro cuvette (optical path length 1 cm). The semimicro cuvette also receives 50 µl of the specimen to be determined (uric acid solution) and 20 µl uricase solution (reaction solution 3).

Actually the combination of reaction mixture and specimen was allowed to stand before the uricase solution was added, in order to permit possible reactions of components of these two solutions to proceed. Only then was the start of the actual reaction induced by addition of the uricase solution. The progress of the reaction was recorded at a wave length of 334 nm with an Eppendorf photometer 1101 and a Phillips Writer (analog device of the firm Eppendorf Instrument Construction GmbH, Hamburg). The reaction was finished after about 3 minutes. The specimen used in this example was an aqueous solution which contained 5,000 µmol/l of uric acid.

Identical results were obtained with aldehyde dehydrogenase E.C. 1.2.1.5. (isolated according to J. F. Clark and W. B. Jakoby, Journal of Biological Chemistry 245, 6065, 1970, or obtained from Sigma Chemical Co., St Louis, Mo. 63178, USA). In these experiments instead of solutions 1 and 4 the following solutions were used:
1. Pyrophosphate potassium chloride buffer: Tetrasodium diphosphate (E. Merck, Darmstadt, Order No. 6591) 0.1 mol/l and potassium chloride (E. Merck, Darmstadt, Order No. 4956) 0.1 mol/l, pH = 8.6.
4. NADP solution (Boehringer-Mannheim GmbH, Order No. 15600) 10 mg/ml.

These analytical procedures are presented only by way of example. The procedure which is the subject of our invention is applicable with any solution of hydrogen peroxide and any substance which can be converted by chemical reaction accompanied by the formation of hydrogen peroxide.

We claim:
1. In a procedure for the rapid quantitative determination of hydrogen peroxide concentration in a biologi- cal medium in an aqueous solution containing other substances which occasionally or frequently cause interference reactions, a process for accurately making such determination without encountering such interference, which process comprises (a) reacting the hydrogen peroxide in the aqueous solution in the presence of the catalyst catalase with ethanol in a manner to cause the formation of acetaldehyde, (b) simultaneously in the same reaction medium reacting the latter in the presence of an aldehyde dehydrogenase as a catalyst, with the oxidized form of nicotinamide-adenine-dinucleotide (NAD) or nicotinamide-adenine-dinucleotide-phosphate (NADP) in a manner to reduce said oxidized form to produce a reduced form identifiable as NADH or NADPH, and (c) determining the concentration of said reduced form in said biological medium aqueous solution.

2. Procedure according to claim 1, characterized by determining the NADH or NADPH concentration photometrically.

3. Procedure according to claim 1 characterized by determining the hydrogen peroxide concentration in an aqueous solution in which uric acid is catalytically reacted with uricase with formation of hydrogen peroxide.

4. Procedure according to claim 1 characterized by determining the hydrogen peroxide concentration in an aqueous solution in which glucose is reacted catalytically with glucose oxidase with formation of hydrogen peroxide.

5. Procedure according to claim 1 characterized by determining the hydrogen peroxide concentration in an aqueous solution in which cholesterol is reacted catalytically with cholesterol oxidase with hydrogen peroxide formation.

6. Procedure according to claim 1 characterized by determination of hydrogen peroxide concentration in an aqueous solution in which the cholesterol ester is reacted catalytically with cholesterol esterase and the cholesterol formed is catalytically converted with cholesterol oxidase with formation of hydrogen peroxide.

7. Procedure according to claim 1 characterized by preliminarily carrying out the formation of hydrogen peroxide from a starting material to be analyzed and subsequently and in the same reaction medium carrying out said reaction of said hydrogen peroxide with ethanol and the reaction of the resulting acetaldehyde with NAD or NADP.

* * * * *